United States Patent [19]

Chen et al.

[11] Patent Number: 5,210,223
[45] Date of Patent: May 11, 1993

[54] ELEVATED PRESSURE PHTHALIC ANHYDRIDE PROCESS

[75] Inventors: Michael S. Chen, Zionsville; Philip J. Cook, Schnecksville; Harold H. Gunardson, New Tripoli, all of Pa.; Melinda B. Ulrich, Annandale, N.J.

[73] Assignee: Air Products and Chemicals, Inc., Allentown, Pa.

[21] Appl. No.: 899,797

[22] Filed: Jun. 17, 1992

[51] Int. Cl.$^5$ .............................................. C07D 307/89
[52] U.S. Cl. ................................. 549/247; 549/248; 549/250
[58] Field of Search ....................... 549/247, 248, 250

[56] References Cited

U.S. PATENT DOCUMENTS

| | | | |
|---|---|---|---|
| 2,064,468 | 12/1936 | Foster | 260/123 |
| 2,076,033 | 4/1937 | Kniskern | 260/123 |
| 2,555,287 | 5/1951 | Hadden | 183/120 |
| 2,574,644 | 11/1951 | Landau | 260/342.5 |
| 2,702,091 | 2/1955 | Smith, Jr. | 183/119 |
| 3,040,051 | 6/1962 | Jubb | 260/296 |
| 3,112,324 | 11/1963 | Foucar | 260/346.4 |
| 4,215,056 | 7/1980 | Schroeder et al. | 549/247 |
| 4,879,387 | 11/1989 | Hara | 549/248 |
| 5,126,463 | 6/1992 | Ramachandrau et al. | 549/248 |

FOREIGN PATENT DOCUMENTS 1158051  11/1963  Fed. Rep. of Germany .

Primary Examiner—Cecilia Tsang
Attorney, Agent, or Firm—Robert J. Wolff; James G. Simmons; Willam F. Marsh

[57] ABSTRACT

The present invention is an improvement to the conventional process for the production of phthalic anhydride. In particular, the present invention enables the crude phthalic anhydride product to be recovered in a more efficient manner.

2 Claims, 3 Drawing Sheets

ELEVATED PRESSURE PHTHALIC ANHYDRIDE PROCESS

FIELD OF THE INVENTION

The present invention relates to a process for the production of phthalic anhydride.

BACKGROUND OF THE INVENTION

Phthalic anhydride is a useful intermediate chemical for making plasticizers, polyester resins and alkyd resins. It is commercially produced by a low pressure vapor-phase air oxidation process known as the von Heyden process. In this conventional process, either o-xylene or naphthalene is oxidized over a vanadium pentoxide/titanium dioxide catalyst contained in fixed bed reactors. Crude phthalic anhydride is recovered from the reactor effluent primarily as a solid by condensing it in multiple switch condensers.

There is a problem in the above-described conventional process relating to the recovery of the crude phthalic anhydride primarily as a solid in the multiple switch condensers. In particular, the problem is that switch condensers are expensive to build (as much as 20-30% of the total capital cost of the process is in the switch condenser section) and, due to solid dusting and plugging in the tubes, troublesome to operate and maintain.

Most of the prior suggestions to remedy the above problem focus on improving the switch condenser designs. U.S. Pat. No. 2,076,033 may be the earliest patent which discusses an improved switch condenser design. Other suggestions focused on eliminating the switch condenser entirely and include: continuous condensation and collection of the phthalic anhydride as a dust (U.S. Pat. No. 2,064,468) or as a slurry (U.S. Pat. No. 2,555,287); scrubbing the gas with a solvent, e.g., dibutyl phthalate (U.S. Pat. No. 2,574,644); using a moving bed of pebbles (U.S. Pat. No. 2,702,091); direct contact with a liquid coolant such as $C_nH_{2n+1}$ (U.S. Pat. No. 3,040,059); cooling the gas by vaporization of naphthalene (U.S. Pat. No. 3,112,324); finally compressing the cooled gas to 2-6 atmospheres and re-cooling it to recover the phthalic anhydride as liquid (German patent 1,158,051). None of these prior suggestions are commercially practiced today however. Indeed, switch condensers are still used exclusively in the present day phthalic anhydride processes and the industry continues to bear the high cost of the switch condenser and the problems associated with its operations and maintenance.

It is an object of the present invention to eliminate the problem of the conventional phthalic anhydride process relating to the recovery of the crude phthalic anhydride as a solid in the multiple switch condensers.

SUMMARY OF THE INVENTION

The present invention is an improvement to a process for the production of phthalic anhydride. In the process to which the improvement pertains, a feed stream comprising oxygen, o-xylene and/or naphthalene is introduced into a reactor to produce a gaseous reactor effluent comprising the phthalic anhydride. Also in the process to which the improvement pertains, the reactor effluent is cooled in order to condense a crude phthalic anhydride product from the reactor effluent wherein at least a portion of the crude phthalic anhydride product is condensed as a solid. The improvement comprises operating the reactor at a pressure greater than 200 psia in order to condense the crude phthalic anhydride product from the reactor effluent exclusively as a liquid.

DETAILED DESCRIPTION OF THE INVENTION

Figure 1:
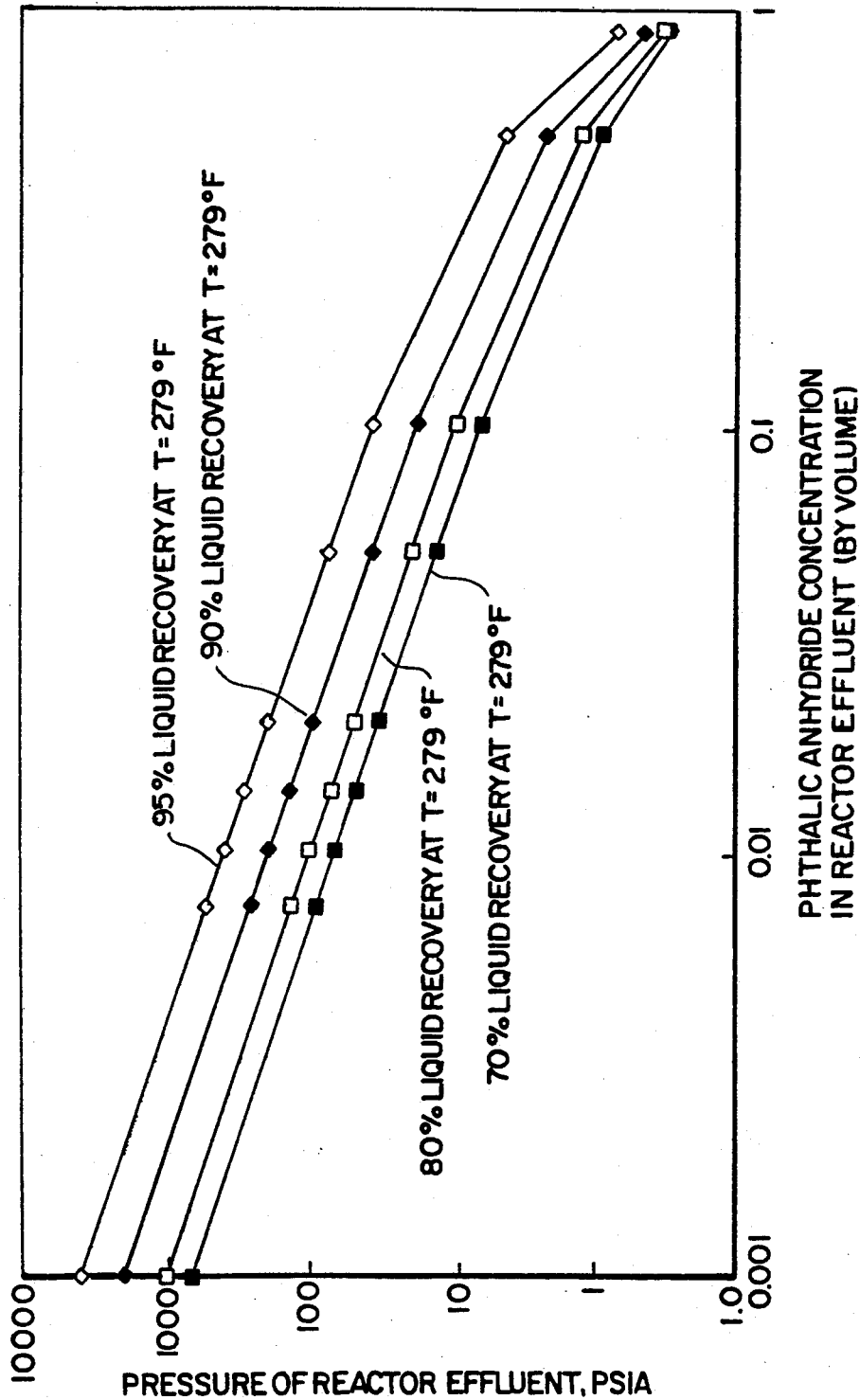
FIGS. 1 and 2 are graphs illustrating the relationship of the present invention's elevated operating pressure to other operating variables in the phthalic anhydride process.

To better understand the present invention, it is important to understand the prior art with respect to phthalic anhydride production and recovery. Phthalic anhydride is commercially produced by a low pressure vapor-phase air oxidation process known as the von Heyden process. In this conventional process, either o-xylene or naphthalene is oxidized over a vanadium pentoxide/titanium dioxide catalyst contained in fixed bed reactors. Where o-xylene is used as the feedstock, typical loadings in the conventional process are 40-130 grams per normal cubic meter of air. The reactor exit temperature is typically about 700°-720° F. while the reactor pressure is about 20-30 psia. The conversion of the feedstock is virtually complete but the selectivity to phthalic anhydride is only 78%. The remaining feedstock is converted to other side reaction products including about 3.5% maleic anhydride and 18.5% carbon dioxide and water. A large amount of exothermic heat of reaction is removed from the reactor by indirect heat exchange through the tube walls with a circulating molten salt which in turn is used to generate useful steam.

Based on the values for the loading, conversion and selectivity discussed above, the concentration of phthalic anhydride in the reactor effluent will be 0.6-2.0% by volume. The remainder of the reactor effluent will be primarily unreacted oxygen and unreactive/inert nitrogen. Crude phthalic anhydride is recovered from the reactor effluent primarily as a solid by condensing it in multiple switch condensers that operate alternately on cooling and heating cycles. Molten crude phthalic anhydride is removed from the switch condenser surfaces on the heating cycle. The reason the crude phthalic anhydride is recovered primarily as a solid is that, at the conditions of the conventional process, one must cool the reactor effluent well below the melting point of phthalic anhydride (267.8° F.) in order to achieve the typical 95% plus recovery.

The crude phthalic anhydride is further purified by heat treating and distillation in the downstream process. Off-gas from the switch condensers containing trace amounts of phthalic anhydride and maleic anhydride etc. is scrubbed with a circulating water solution to produce a liquid byproduct containing these trace amounts and a scrubbed gas. The scrubbed gas is then incinerated with a fuel gas before venting it to the atmosphere. Optionally, a portion of the scrubbed gas can be recycled as feed to the reactor in order to dilute the feedstock loading since high feedstock loadings increase flammability problems in the reactor area.

There is a problem in the above-described conventional process relating to the recovery of the crude phthalic anhydride primarily as a solid in the multiple switch condensers. In particular, the problem is that switch condensers are expensive to build (as much as 20-30% of the total capital cost of the process is in the switch condenser section) and, due to solid dusting and plugging in the tubes, troublesome to operate and maintain.

The present invention eliminates the above problem by elevating the operating pressure of the reactor to at least 200 psia in order to condense the crude phthalic anhydride product from the reactor effluent *exclusively as a liquid* in a continuous condenser at temperatures above its melting point. Expensive and trouble-some switch condensers are eliminated.

The skilled practitioner will appreciate that optimization of the 200 psia minimum operating pressure will depend on the following operating variables:

(1) The desired recovery rate which is the percentage of the phthalic anhydride in the reactor effluent which is condensed out of the reactor effluent to form the crude phthalic anhydride product;

(2) The phthalic anhydride concentration in the reactor effluent; and (3) The temperature above the melting point of phthalic anhydride at which the condensation is carried out.

The present invention's lower pressure limit of 200 psia is based on a 95% recovery rate, a 2.0% (by volume) phthalic anhydride concentration in the reactor effluent and a 279° F. condensation temperature. The 95% recovery rate and 2.0% phthalic anhydride concentration represent typical values in the conventional process. The 279° F. condensation temperature allows for a sufficient safety margin above the melting point of phthalic anhydride to ensure that no solid phthalic anhydride is formed.

Figure 2:
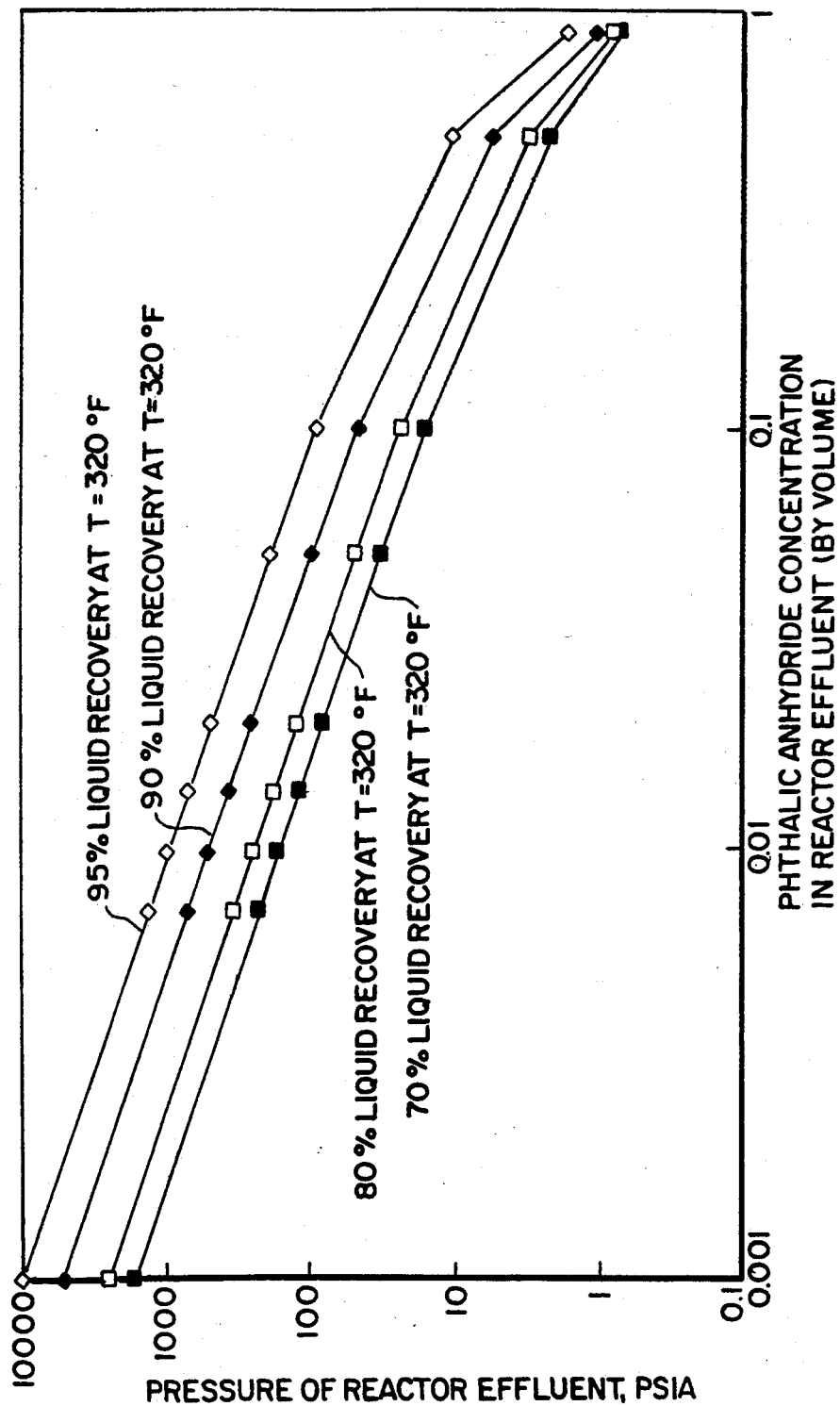

To assist the skilled practitioner in optimizing the 200 psia minimum operating pressure for different recovery rates, phthalic anhydride concentrations and condensation temperatures, FIGS. 1 and 2 are provided. FIG. 1 is a graph which enables one to optimize the 200 psia minimum operating pressure (shown on FIG. 1 as the pressure of the reactor effluent) for: (1) a condensation temperature of 279° F., (2) recovery rates between 70 and 95% and (3) phthalic anhydride concentrations between 0.001 and 0.9 by volume. FIG. 2 is identical to the FIG. 1 graph except the condensation temperature is 320° F. In effect, the FIG. 2 graph shows the sensitivity of the required operating pressure to a higher condensation temperature.

In addition to eliminating the need for multiple switch condensers, other benefits of the present invention's elevated operating pressure include smaller volumetric flow rates, higher kinetic rates and higher heat transfer rates in the bulk gas and tube wall regions of the reactor and condensers. The results are smaller reactor and other equipment sizes, more efficient heat removal rates, and a more uniform temperature profile along the reactor tube length to minimize the hot spot and runaway potentials. Higher kinetic rates also permit the reactor to be run at lower temperature such that selectivity to the main product, phthalic anhydride, is increased. To illustrate this last point, it is useful to examine the following kinetic rate expressions pursuant to the article by J. C. Pirkle Jr., et al., "Activity profiling in catalyst reactors", *Chemical Engineering Progress,* August, 1987):

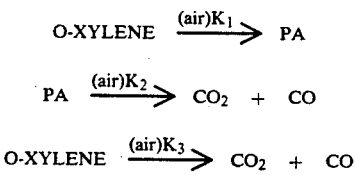

$Rate_1 = K_1 \cdot P_{OX} \cdot P_{O2}$; ln $K_1 = -13,588/T + 11.597$ (main reaction)
$Rate_2 = K_2 \cdot P_{PA} \cdot P_{O2}$ ln $K_2 = -15,601/T + 12.619$ (side reaction)
$Rate_3 = K_3 \cdot P_{OX} \cdot P_{O2}$ ln $K_3 = -14,394/T + 10.730$ (side reaction)

where T is temperature in degrees Kelvin; K is the rate constant and $P_{OX}$, $P_{O2}$ and $P_{PA}$ is the pressure in MPa (1,000,000 pascal) for the o-xylene, the oxygen (via the air) and the phthalic anhydride respectively.

Since the main reaction has lower activation energy than the two side reactions, lower operating temperatures should lead to higher selectivity to phthalic anhydride. For example, the selectivities, expressed as $R_1/R_2$ and $R_1/R_3$, at 650° F., are about 3 times higher than those at 720° F. as evident from the results of the following calculations:

| 720° F. | 650° F. |
|---|---|
| $R_1 = 769.6$ | $R_1 = 563.2$ |
| $R_2 = 0.00001396$ | $R_2 = 0.00000311$ |
| $R_3 = 0.00001331$ | $R_3 = 0.00000333$ |
| $R_1/R_2 = 55,130,000$ | $R_1/R_2 = 181,000,000$ |
| $R_1/R_3 = 57,820,000$ | $R_1/R_3 = 169,000,000$ |

Thus, by operating the reactor at higher pressure, all rates are increased by the square of the pressure ratio (as suggested by the rate expressions above) so that the reactor can be operated at lower temperature without sacrificing productivity. Consequently, the selectivity of the main product is increased resulting in improved overall process efficiency, lower equipment costs and reduced feed stock consumption.

Figure 3:
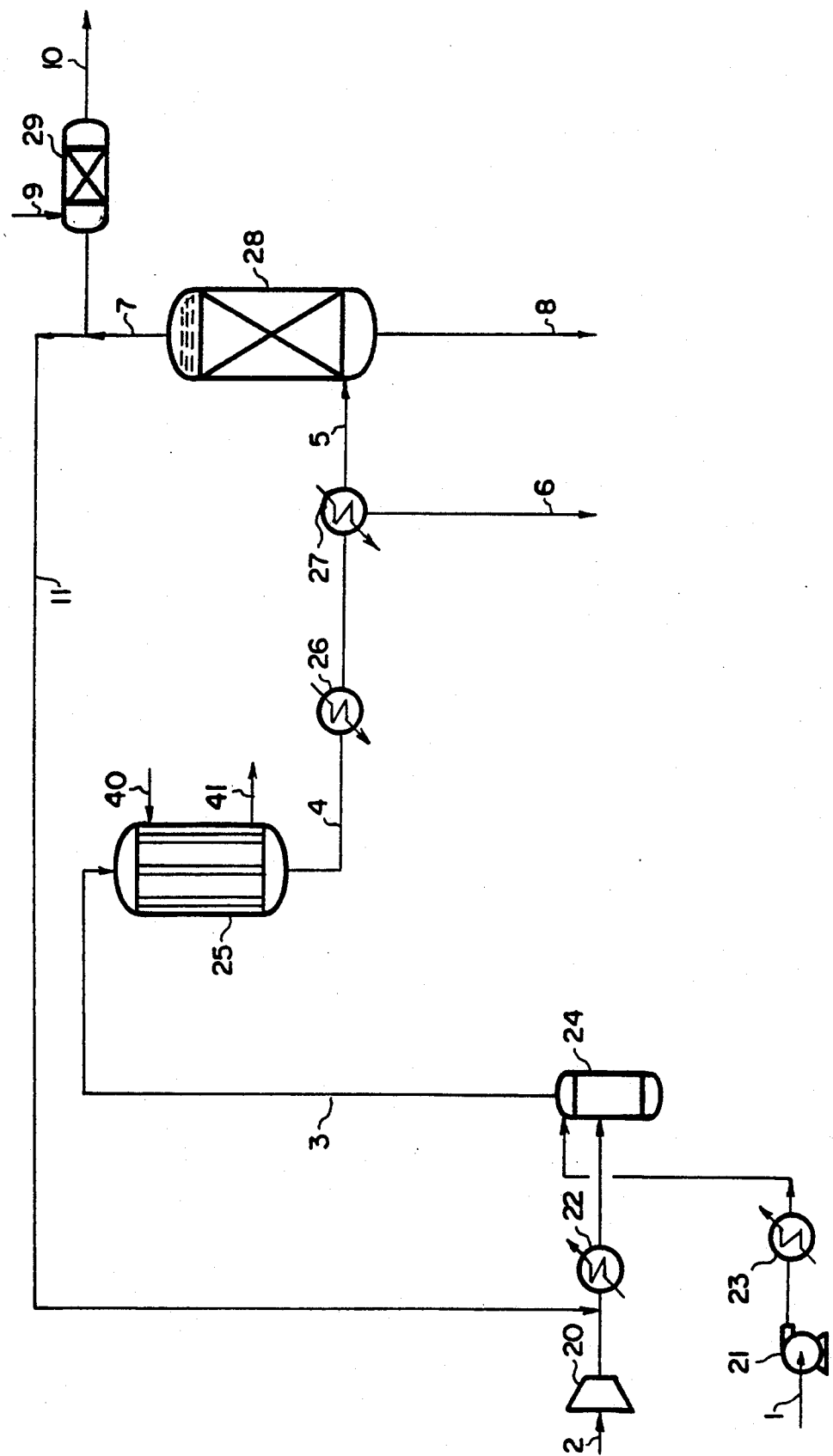
FIG. 3 is a process flowsheet illustrating one embodiment of the present invention.

FIG. 3 illustrates one embodiment of the present invention. Oxygen feed stream 2 is compressed in compressor 20, preheated in heater 22, mixed with recycle stream 11 and finally mixed in evaporator 24 with ortho-xylene that has been pumped in pump 21 and preheated in preheater 23. The skilled practitioner will appreciate that an oxygen feed stream is used instead of an air feed stream in order to save on compression costs. The completely vaporized reactor feed 3 passes to reactor 25 where the ortho-xylene is converted to phthalic anhydride, organic by-products, and carbon oxides. Reaction heat is absorbed by circulating molten salt via streams 40 and 41. The reactor effluent 4 is cooled first in a high-pressure steam superheater 26 and subsequently in an economizer condenser 27 wherein the crude phthalic anhydride product is condensed as stream 6. The uncondensed gases in stream 5 are fed to a scrubber 28 wherein the uncondensed gases are scrubbed with water to form a scrubbed gas in stream 7 and a by-product liquor in stream 8. A portion of the scrubbed gas is recycled to the oxygen feed stream as stream 11 in order to dilute the feedstock loading which will be higher than usual since an oxygen feed is being used instead of an air feed. (Recall that high feedstock loadings increase flammability problems in the reactor area). The remaining portion of the scrubbed gas stream is subsequently fed to a catalytic incinerator 29 wherein said remaining portion is incinerated in the presence of a fuel gas from stream 9. The combustion products are then vented to the atmosphere in stream 10. Operating conditions for the streams shown in FIG. 3 are included in the following Table 1. Also calculated and shown in Table 1 is the o-xylene loading in reactor feed stream 3, the percentage of phthalic anhydride which is recovered in stream 6 and the horsepower for compressing oxygen feed stream 2.

produce a gaseous reactor effluent comprising the phthalic anhydride; and (b) cooling the reactor effluent in order to condense a crude phthalic anhydride product from the reactor effluent wherein at least a portion of the crude phthalic anhydride product is condensed as a solid; the improvement comprising operating the reactor in step (a) at a pressure greater than 200 psia in order to

TABLE 1

| | STREAM NO. | | | | |
|---|---|---|---|---|---|
| | 1 | 2 | 3 | 4 | 5 |
| | STREAM NAME | | | | |
| | O-XYLENE FEED | OXYGEN FEED | REACTOR FEED | REACTOR EFFLUENT | ECONOMIZER CONDENSER EFFLUENT |
| TEMPERATURE, F. | 80.00 | 70.00 | 248.23 | 720.00 | 278.60 |
| PRESSURE, PSIA | 16.00 | 14.70 | 389.00 | 380.00 | 376.00 |
| FLOWRATE, LB-MOLES/HR | 247.00 | 1149.95 | 13,897.00 | 13,961.20 | 13,554.50 |
| FLOWRATE, FT3/HR | N/A | 444,874 | 271,485 | 465,180 | 285,696 |
| VOLUME, % | | | | | |
| NITROGEN | 0.00 | 0.00 | 0.00 | 0.00 | 0.00 |
| ARGON | 0.00 | 0.50 | 1.27 | 1.26 | 1.30 |
| OXYGEN | 0.00 | 99.50 | 18.35 | 10.41 | 10.72 |
| WATER | 0.00 | 0.00 | 0.77 | 6.72 | 5.40 |
| CARBON DIOXIDE | 0.00 | 0.00 | 77.84 | 80.10 | 82.50 |
| O-XYLENE | 100.00 | 0.00 | 1.78 | 0.00 | 0.00 |
| MALEIC ANHYDRIDE | 0.00 | 0.00 | 0.00 | 0.12 | 0.03 |
| PHTHALIC ANHYDRIDE | 0.00 | 0.00 | 0.00 | 1.38 | 0.05 |
| FUEL GAS, METHANE | 0.00 | 0.00 | 0.00 | 0.00 | 0.00 |
| XYLENE LOADING, gr/Nm$^3$ | | | 84.00 | | |
| % LIQUID PAN CONDENSED at 278.6° F. | | | | | |
| OXYGEN COMPRESSOR, HP | | 2346.00 | | | |

| | STREAM NO. | | | | | |
|---|---|---|---|---|---|---|
| | 6 | 7 | 8 | 9 | 10 | 11 |
| | STREAM NAME | | | | | |
| | CRUDE PHTHALIC ANHYDRIDE | SCRUBBED GAS | BY-PRODUCT LIQUOR | FUEL GAS | VENT GAS | RECYCLE GAS |
| TEMPERATURE, F. | 278.60 | 135.61 | 193.49 | 80.00 | 804.85 | 135.61 |
| PRESSURE, PSIA | 376.00 | 373.00 | 376.00 | 376.00 | 373.00 | 373.00 |
| FLOWRATE, LB-MOLES/HR | 406.66 | 12,921.50 | 633.37 | 9.00 | 430.50 | 12,500.00 |
| FLOWRATE, FT3/HR | N/A | 221,395 | N/A | 139 | 15,664 | 214,174 |
| VOLUME, % | | | | | | |
| NITROGEN | 0.00 | 0.00 | 0.00 | 0.00 | 0.00 | 0.00 |
| ARGON | 0.00 | 1.36 | 0.00 | 0.00 | 1.33 | 1.36 |
| OXYGEN | 0.00 | 11.25 | 0.00 | 0.00 | 6.83 | 11.25 |
| WATER | 50.78 | 0.85 | 98.25 | 0.00 | 5.01 | 0.85 |
| CARBON DIOXIDE | 0.03 | 86.54 | 0.14 | 0.00 | 86.82 | 86.54 |
| O-XYLENE | 0.00 | 0.00 | 0.00 | 0.00 | 0.00 | 0.00 |
| MALEIC ANHYDRIDE | 3.37 | 0.00 | 0.58 | 0.00 | 0.00 | 0.00 |
| PHTHALIC ANHYDRIDE | 45.76 | 0.00 | 1.04 | 0.00 | 0.00 | 0.00 |
| FUEL GAS, METHANE | 0.00 | 0.00 | 0.00 | 100.00 | 0.00 | 0.00 |
| XYLENE LOADING, gr/Nm$^3$ | | | | | | |
| % LIQUID PAN CONDENSED at 278.6° F. | | 96.60 | | | | |
| OXYGEN COMPRESSOR, HP | | | | | | |

The present invention has been described with reference to a specific embodiment thereof. This embodiment should not be viewed as limitation to the present invention, the scope of which should be ascertained by the following claims.

We claim:

1. In a process for the production of phthalic anhydride comprising the consecutive steps of:
   (a) introducing a feed stream comprising oxygen and either o-xylene or naphthalene into a reactor to produce a gaseous reactor effluent comprising the phthalic anhydride; and
   (b) cooling the reactor effluent in order to condense a crude phthalic anhydride product from the reactor effluent wherein at least a portion of the crude phthalic anhydride product is condensed as a solid; the improvement comprising operating the reactor in step (a) at a pressure greater than 200 psia in order to condense the crude phthalic anhydride product from the reactor effluent in step (b) exclusively as a liquid.

2. The process of claim 1 wherein subsequent to step (b), the process further comprises:
   (c) scrubbing the portion of the reactor effluent which is not condensed in step (b) to produce a liquid byproduct and a scrubbed gas;
   (d) recycling a portion of the scrubbed gas to the reactor;
   (e) incinerating the remaining portion of the scrubbed gas in the presence of a fuel gas to produce a vent gas.

* * * * *